United States Patent [19]

Tokitoh et al.

[11] 4,271,320
[45] Jun. 2, 1981

[54] PROCESS FOR PRODUCING A HIGHER CARBONYL COMPOUND

[75] Inventors: Yasuo Tokitoh; Noriaki Yoshimura; Masuhiko Tamura, all of Kurashiki, Japan

[73] Assignee: Kuraray Co., Ltd., Kurashiki, Japan

[21] Appl. No.: 71,670

[22] Filed: Aug. 31, 1979

[30] Foreign Application Priority Data

Sep. 5, 1978 [JP] Japan ............... 53-109237
Sep. 5, 1978 [JP] Japan ............... 53-109238

[51] Int. Cl.³ .................. C07C 45/34; C07C 45/36; C07C 29/136; C07C 29/14; C07C 45/27
[52] U.S. Cl. .................. 568/426; 568/431; 568/47,; 568/320; 568/360; 568/401; 568/814; 568/880; 568/881
[58] Field of Search ............... 260/586 P, 597 B, 599, 260/604 HF; 568/715, 880, 881, 814, 426, 431, 475, 401, 320, 360

[56] References Cited

U.S. PATENT DOCUMENTS

| | | | |
|---|---|---|---|
| 3,104,263 | 9/1963 | Riemenschneider et al. | 260/597 B |
| 3,122,586 | 2/1964 | Berndt et al. | 260/597 B |
| 3,154,586 | 10/1964 | Bander et al. | 568/401 |
| 3,301,905 | 1/1967 | Riemenschneider et al. | 260/597 B |
| 3,461,157 | 8/1969 | Olivier et al. | 260/604 AC |
| 3,499,938 | 3/1970 | Hwang et al. | 568/880 |
| 3,708,549 | 1/1973 | Reifenberg et al. | 568/880 |
| 3,932,521 | 1/1976 | Gloyer et al. | 260/597 B |
| 4,085,145 | 4/1978 | Mimoun | 260/597 B |
| 4,152,354 | 5/1979 | Stapp | 260/586 P |

OTHER PUBLICATIONS

Clement et al., J. Org. Chem., vol. 29, pp. 241–243 (1964).
Fahey et al., J. Org. Chem., vol. 39, pp. 3276–3277 (1974).
Lapinta et al., Tet. Lett., pp. 3817–3820 (1977).
Okoda et al., J. Chem. Soc. Japan, Indust. Chem. Section, vol. 69, pp. 2137–2141 (1966).
Hrusovsky et al., Chem. Abst., vol. 76, #33736s (1972).
Gaylord, "Polyethers", pp. 239–241 (1963).

*Primary Examiner*—Natalie Trousof
*Assistant Examiner*—James H. Reamer
*Attorney, Agent, or Firm*—Barry Kramer

[57] ABSTRACT

An industrially suitable process for producing a higher carbonyl compound by the oxidation of an olefinic compound having at least six carbon atoms is provided. Said improved process comprises oxidizing the olefinic compound in aqueous medium containing palladium or salt thereof and a copper salt in the presence of a specific water-soluble polyoxyalkylene compound in an amount of from about ¼ to about 3 parts by weight per 1 part by weight of water contained in the reaction mixture. The improvement is demonstrated in terms of yield, selectivity, separation of the product, and recycle of the catalyst.

13 Claims, No Drawings

PROCESS FOR PRODUCING A HIGHER CARBONYL COMPOUND

BACKGROUND OF THE INVENTION

1. Field of the Invention

The present invention relates to an improvement in a process for producing carbonyl compounds having at least 6 carbon atoms which comprises oxidizing a corresponding olefinic compound in aqueous medium containing palladium or salt thereof and a copper salt.

2. Description of the Prior Art

A method of producing carbonyl compounds by contacting olefinic compounds with aqueous medium containing palladium or its salt as a main catalyst component is well known as aqueous Wacker oxidations (for example, U.S. Pat. Nos. 3,122,586 and 3,154,586). An industrial application of this reaction is now seen in the production of acetaldehyde and acetone from ethylene and propylene respectively. Said oxidation is in general carried out in the presence of a redox promotor as a co-catalyst represented by a copper salt in view of effective utilization of such an expensive palladium catalyst. This reaction is carried out, in a gaseous atmosphere with or without oxygen. The latter case is called the "two step method", because there is required an additional step to reoxidize the reduced catalyst component with oxygen-containing gas for reuse of said component. On the other hand the former is called the "single step method", because the reoxidation step is not always necessary. An advantage of the two step method is that undesirable side reactions due to oxygen can be avoided and therefore it is in particular preferably applicable in cases where the reaction products (e.g. aldehydes) are chemically unstable to oxygen.

An olefinic compound having at least 6 carbon atoms in the molecule is relatively insoluble in water. Accordingly, for the purpose of producing the corresponding carbonyl compound from said olefinic compound by the abovementioned reaction, it has been considered necessary to (1) dissolve the olefinic compound in the reaction system by using water-soluble polar solvents such as dimethylformamide, dimethylacetamide, hexamethylphosphoric triamide, dimethylsulfoxide, sulfolane, dioxane or tetrahydrofuran in combination with water [J. Org. Chem., 29, 241 (1964) and 39, 3276 (1974)] or (2) disperse the olefinic compound in water by adding a suitable amount of cationic or nonionic surfactant to the reaction system [Tetrahedron Letters, 3817-3820 (1977)]. When industrial operation is intended, however, it may be poined out that such a reaction is accompanied with enormous troubles. Thus, the above method (1) involves the following problems: (a) in the case that the two step method is adopted, palladium metal partially precipitates and deposits on the wall of a reactor in the oxidation, whereby a problem on process engineering takes place; (b) the reaction system becomes chemically unstable, because many water-soluble polar solvents are susceptible to partial hydrolysis under oxidative conditions; (c) a lot of steam is required due to the presence of a polar solvent and such a solvent is contaminated into the distillate in separating and recovering the product by steam distillation; (d) solvent-extraction for the separation of the product requires a large amount of the extracting solvent, and the distribution coefficient of such a polar solvent and catalyst component into the extracting layer is so high that separation of the product and recycle of the catalyst become troublesome. Further, the above method (2) involves the following problems: (a) deposition of metallic palladium on the reactor wall is apt to take place when the two step method is employed; (b) foaming is apt to take place in separation of the product by steam distillation; (c) a vague interface is observed between an aqueous layer and an organic layer in extracting the product with a solvent; and (d) the reaction velocity is lower than in the method (1).

SUMMARY OF THE INVENTION

Accordingly, a primary object of the present invention is to prepare a carbonyl compound having at least 6 carbon atoms from a corresponding olefinic compound while avoiding the various problems above described. Another object of the invention is to carry out the reaction without using such a water-soluble polar solvent or surfactant which is inevitably accompanied by the above various problems. A further object of this invention is to provide a process for preparing said carbonyl compound in an industrially appropriate manner.

These and other objects can be attained according to the present invention by oxidizing an olefinic compound having at least 6 carbon atoms in aqueous medium containing palladium or its salts and a copper salt in the presence, for each 1 part by weight of water, of about ¼ to about 3 parts by weight of a water-soluble polyoxyalkylene compound represented by the general formula:

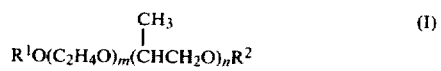

wherein $R^1$ and $R^2$ are the same or different and each represents a hydrogen atom or a hydrocarbon radical containing 1-8 carbon atoms, m is an integer greater than 0, and n is zero or an integer greater than zero, such that $m+n \geq 4$ and $m > 3n$.

According to the process of the present invention, there can be attained a marked improvement in reaction rate, selectivityy of reaction, easier product separation, easier separation and recycle of the catalyst solution, and broad applicability to various olefinic compounds. Thus higher carbonyl compounds can be produced effectively on an industrial scale according to the said oxidation of the present invention.

DETAILED DESCRIPTION OF THE INVENTION

The polyoxyalkylene compound of formula (I) used in the present invention should be water-soluble for attaining the desired effect. The term "water-soluble" herein means that the compound is soluble in water in almost spontaneous ratio in the range of temperature from room temperature to about 110° C. The solubility in water of the polyoxyalkylene compound (I) depends on the total carbon number in $R^1$ and $R^2$, $m+n$ value and n/m value. As $m+n$ value is bigger and/or n/m value is smaller, solubility of the compound (I) becomes complete even if the carbon number in $R^1$ and $R^2$ were large. Therefore, the type of $R^1$ and $R^2$ should be selected so as to render the polyoxyalkylene compound water-soluble. As far as the water-solubility is concerned, it is adequate that at least one of $R^1$ and $R^2$, but preferably each of them, is a hydrogen atom. Considering ease of product recovery, it is preferred that both of $R^1$ and $R^2$ are hydrogen atoms or hydrocarbon groups containing 1 to 8 carbon atoms such as methyl, ethyl, propyl, butyl, pentyl, hexyl, phenyl, tolyl, cyclohexyl, and like groups. In case that both of $R^1$ and $R^2$ are hydrocarbon groups, it is preferable to employ the same or different hydrocarbon groups containing not more than about 10 total carbon atoms. Alkyl groups containing 1 to 5 carbon atoms, such as methyl, ethyl, propyl and butyl groups are especially preferred. The polyoxyalkylene compound may be used alone or in admixture of two or more different types.

In the general formula (I) representing the polyoxyalkylene compound used in the present invention, m denotes a unit number of the oxyethylene groups and is an integer greater than zero, n denotes a unit number of the oxypropylene groups and zero or an integer greater than zero, the total value of m and n should be at least 4 (namely $m+n \geq 4$), and the ratio of n to m should be less than $\frac{1}{3}$ (namely $m > 3n$). Where the value of $m+n$ is less than 4, no improvement in recovery of the product may be expected. In more detail, when the value of $m+n$ is less than 4, and the product and unreacted material are recovered from the reaction mixture by steam distillation, the polyoxyalkylene compound is brought into the product in the distillate and results in a complicated separation of the product from the contaminant polyoxyalkylene compound. Alternatively, when the value of $m+n$ is less than 4 and the product is recovered by extraction with a solvent, the polyoxyalkylene compound ($m+n<4$), accompanied by the catalyst component, is distributed into the extract layer and an additional separation operation is required and recycle of a catalyst component becomes difficult.

By using a polyoxyalkylene compound wherein $m+n$ value is at least 4, the deposit of a reduced catalyst component such as palladium black on the wall of a reactor can be avoided successfully. Thus, the separation and recycle of the catalyst can be simplified in the oxidation reaction of the present invention where the use of the two-step method or a low rate of oxygen supply in the one step method would normally cause reduced catalyst component to deposit on the reactor wall. The upper limit of $m+n$ value is not so critical as the lower limit. A preferred $m+n$ value is not more than about 100 mainly in view of availability, operability and the reaction results. Ratio of n to m (n/m) in the polyoxyalkylene compound (I) used in this invention is not more than $\frac{1}{3}$, as described above. A polyoxyalkylene compound having the ratio $n/m \geq \frac{1}{3}$ exhibits a reduced water solubility or a decreased oxidation stability in many cases. Further, a polyoxyalkylene compound of $m > 3n$ is apt to be extracted together with a catalyst component when the solvent-extraction is employed for the separation of the product from the reaction mixture, and said polyoxyalkylene compound decreases the solubility and dispersibility of a catalyst component. Thus, it is more preferable to use a polyoxyethylene compound ($n=0$), and most preferable to use a polyoxyethylene glycol, wherein m is 6–75, and $C_1$–$C_5$ alkyl ethers thereof, such as monomethyl ether, dimethyl ether, methyl ethyl ether and diethyl ether are particularly preferred.

Improvement in the reaction rate, selectivity of the reaction, solubility of a catalyst component and separation and recovery of the product in the invention also depends upon the amount of the polyoxyalkylene compound in addition to the above-mentioned relation of m and n. It is significant in this respect to use the polyoxyalkylene compound in an amount of about $\frac{1}{4}$ to about 3 parts by weight per 1 part by weight of water existing in the reaction system, namely in the form of an aqueous solution at a concentration of about 20 to about 75% by weight. Reaction rate and/or selectivity will become insufficient if the amount of the polyoxyalkylene compound is too small. On the other hand, solubility of a catalyst component and/or separation and recovery of the product and the unreacted material from the reaction mixture will become insufficient if said amount is too much.

The oxidation reaction per se can be carried out in almost the same manner as in "aqueous Wacker oxidations", except that a specific amount of the polyoxyalkylene compound is added. Palladium or a salt thereof will be used as a main catalyst component in the present invention, and preferably includes palladium metal (oxidized under the reaction conditions into palladium (II)), palladium chloride, palladium bromide, palladium nitrate, palladium acetate, palladium-lithium chloride, and palladium-sodium chloride. Said catalyst component is used in an amount of 0.001 to 0.5 mole, preferably 0.01 to 0.5 mole per liter of the reaction mixture. Copper salts used as redox promoters include cuprous and cupric salts. Preferred examples are cuprous chloride, cupric chloride, cuprous bromide, cupric bromide, cupric acetate, and cupric nitrate. These copper salts may be used singly or in combination of two or more sorts. An appropriate concentration of a redox promoter in the reaction system ranges from 1 to 50 in terms of atomic ratio of copper to palladium from the point of reaction rate and selectivity of the reaction.

Reaction rate and selectivity of the reaction are also influenced by the kind and concentration of anions contained in the reaction system. It is desirable in this respect to use 4 to 100 equivalents, preferably 5 to 75 equivalents, of chloride ions (particularly preferred) or bromide ions per 1 atom of palladium. These anions may be added in general to the reaction system in the form of palladium and copper salts, but the total or a part of the required amount thereof may be added in the form of a corresponding mineral acid or an alkali- or alkaline earth metal salt of the corresponding mineral acid.

The oxidation of the present invention may be carried out in a batch or continuously in a reaction apparatus as generally used for the known gas-liquid reaction. Depending upon the reaction conditions, metallic palladium or a salt of a metal of lower valency may partially precipitate, resulting in deposition on the wall of a reactor. A reactor equipped with a stirrer is the most desirable in view of avoiding the deposition. This oxidation may be carried out at a temperature from room temperature to about 150° C. but practically at about 40° to about 110° C., especially 60° to 95° C. in consideration of reaction rate, selectivity of the reaction and stability of the polyoxyalkylene compound against oxiation.

The olefinic compound used in the present invention for preparing the corresponding carbonyl compound means a group of compounds containing 6 or more carbon atoms preferably up to 30 carbon atoms and having at least one $-CH=CH_2$ group (trminal vinyl group) or $-CH=CH-$ group and forming no stable complex compounds with palladium. Suitable olefinic compounds include mono-olefinic or non-conjugated diolefinic hydrocarbons containing 6 to 25 carbon atoms such as 1-hexene, 1-octene, 2-octene, 3-octene, 1-decene, 1hexadecene, 1-eicocene, 1,7-octadiene, 1,11-dodecadiene, norbornene, 6-methyl-1, 5-heptadiene, 1,15-hexadecadiene, styrene, and alkyl-substituted styrenes. Generally, an olefinic compound having a terminal vinyl group gives the corresponding methyl ketone and an olefinic compound having a —CH=CH— group gives the corresponding ketone. Styrene and alkyl-substituted styrenes such as α-methyl styrene and vinyl toluenes are oxidized according to the invention to produce the corresponding phenylacetaldehydes as main products. According to the known Wacker oxidation technique wherein styrene is oxidized in aqueous solution containing palladium or its salt and copper salts, it is reported that the main product is acetophenone [J. Chem. Soc., Japan, Industrial Section, 69, 2137 (1966)]. In the present invention, however, it is possible to obtain phenyl-acetaldehyde, which is valuable as a raw material for perfumes and an organic synthesis, as the main product. In the case where the desired product is an aldehyde like phenylacetaldehyde which is susceptible to further oxidation by oxygen under the reaction conditions, it should be recommended to employ the one step method under controlled partial pressure of oxygen or the two step method in which oxygen gas is substantially absent in the oxidation system. When ketones are the desired reaction products, the one step method is preferably employed, the ketones are relatively stable to oxygen and the efficiency of the catalyst is improved. A practical partial pressure of oxygen in the one step method is 0.1 to 5.0 atm. (absolute). The oxygen-containing gas used for oxidation of an olefinic compound or for reoxidation of the catalyst component may generally be pure oxygen gas or air, but can optionally be one of these in combination with inert gas such as nitrogen, helium, argon, methane or ethane. Ann olefinic compound may be fed into the reaction system totally at one time at the beginning of the reaction or may be supplied continuously or intermittently in amounts corresponding to the consumption of the olefinic compound during the reaction. Organic solvents may be added to the reaction system on condition that the reaction is not inhibited thereby.

The product can be separated from the reaction mixture by steam distillation or extraction with a solvent, whereby unreacted starting material is distilled or extracted together with the product. Steam distillation may be suitable for the product having 6 to about 12 carbon atoms. Separation of the product having more than 12 carbon atoms by steam distillation is not practical because it requires too much steam. Steam distillation may be carried out in a conventional manner. In a preferable embodiment of the present invention, the steam distillation is conducted while the catalyst is partially reoxidized by introducing a regulated amount of oxygen-containing gas into the reaction mixture. The distillate is separated into aqueous layer and organic layer. Almost all of the aqueous layer is recycled to a distillation apparatus, and the organic layer is further separated into each components by appropriate separating procedures such as distillation, crystallization and the like. The residual aqueous bottom liquid is recycled to the oxidation step, after reoxidation of the catalyst component contained therein, if necessary. Separation of the product by the extraction may be carried out in a conventional manner which comprises contacting the reaction mixture with a substantially water-insoluble organic solvent. The extraction solvent should be selected appropriately in accordance with the distribution coefficient of the unreacted material, product, and polyoxyalkylene compound of formula (I) into the extracted layer, the extraction temperature and the like. Broadly applicable as extracting solvents are hydrocarbons such as butane, pentane, hexane, heptane, octane, cyclohexane, benzene, toluene, xylene, butylbenzene, or dodecylbenzene, and ethers such as diisopropyl ether or dibutyl ether. Some starting materials and/or products can serve as extracting solvents. These extracting solvents may be used alone or in combination, preferably in an amount of 0.5 to 5 parts by volume per 1 part by volume of the oxidation-reaction mixture. The extract layer may be separated into each components by ordinary separating procedures such as distillation or crystallization. Extraction temperature may be selected in the range of temperature from the temperature of the reaction mixture soon after the reaction to room temperature. The aqueous residual layer containing a catalyst component is recycled to the step of oxidation of the olefinic compound, after oxidation treatment of the catalyst component with oxygen if necessary.

A preferable application of the present invention is oxidation of styrene for preparing phenylacetaldehyde. As is well known, phenylacetaldehyde is hydrogenated into β-phenethyl alcohol which is broadly used as a perfume. As above described, styrene has been oxidized by known methods to give acetophenone as a main product, whereby the yield of phenylacetadehyde is low. According to the present invention, however, phenylacetaldehyde can be prepared in high yield and in high selectivity without difficulties in the recycle of a catalyst. Therefore the present invention is appraised to be more appropriate for industrial operation than other methods for preparing phenylacetaldehyde such as isomerization of styrene oxide and dehydration of styrene glycol.

Oxidation of styrene according to the present invention is carried out more preferably in the substantial absence of gaseous oxygen or under limited supply of gaseous oxygen and in the presence of substantially water-insoluble organic solvent. Said organic solvent is considered effective for preventing the thermally induced polymerization of styrene in the reaction system and may be selected from aliphatic hydrocarbons, aromatic hydrocarbons, and ethers. Preferred solvents include aromatic hydrocarbons such as benzene, toluene, xylene, ethylbenzene, or dodecylbenzene and mixed solvents mainly containing the same. The solvent is used genrerally in an amount of 0.25 to 5.0 parts by volume per 1 part by volume of styrene.

Separation of the formed phenylacetaldehyde from the reaction mixture is appropriately carried out by extracting with an organic solvent. The organic solvent used is preferably the same aromatic hydrocarbon as is preferably added to said oxidation system. The residual aqueous layer which contains a polyoxyalkylene compound, palladium or salt thereof and the reduced promoter is combined with an aqueous layer obtained from extraction of the organic layer with water to recover the catalyst components which may be distributed in a slight amount into the said organic layer. The combined aqueous layer is contacted with oxygen-containing gas for the regeneration of the catalyst component. A part of water in the aqueous layer may be removed prior to the treatment with oxygen-containing gas. Treatment with oxygen-containing gas may be carried out at temperature below about 100° C. preferably about 20° to about 100° C. to prevent denaturalization of a polyoxyalkylene compound. Hydrogenation of phenylacetaldehyde into β-phenethyl alcohol can be carried out in the presence of ordinary nickel catalyst such as Raney nickel, modified Raney nickel containing a small amount of chromium, molybdenum, tungsten, rhenium, manganese, titanium or iron, nickel/diatomaceous earth, and nickel/silica. Hydrogenation may be carried out without solvent, but is more practical in the presence of a diluent such as water, alcohol, ester, ether, or aliphatic hydrocarbon. Temperature and hydrogen pressure in hydrogenation can be appropriately in the range of temperature from 10° to 100° C. and 1 to 100 atm, respectively.

Presently preferred and practical embodiments of the present invention are illustratively shown in the following examples.

EXAMPLE 1

Into a 200 ml four-necked flask equipped with a thermometer, a reflux condenser, a stirrer and gas-inlet were supplied distilled water (50 g), $CH_3O(C_2H_4O)_{13}CH_3$ (50 g), palladous chloride (1.0 mmol) and cupric chloride dihydrate (6.0 mmol) and the resultant mixture was heated to 60° C. under stirring. When the inside temperature got to 60° C. constantly, 1-octene (10 ml: 63.8 mmol) was added. Vigorous stirring was continued while oxygen gas was introduced from the gas-inlet at a rate of 5 l/hr. After the reaction for 1 hour, the reaction mixture was assayed by gas chromatographic analysis for determination of the amount (mmol) of 2-octanone formed and the yield of 2-octanone based on the consumed 1-octene (selectively of 2-octanone). Results are shown in Table 1. The formed 2-octanone was separated by subjecting the reaction mixture to steam distillation. The ratio by weight of the distilled water to the distilled 2-octanone (value obtained by dividing the amount of distilled water required for distilling 95% 2-octanone existing in the reaction mixture mixture by the amount of distilled 2-octanone) is shown in Table 1. Separately, the solvent extraction was carried out for the separation of the product using n-hexane as a solvent in an amount by volume equal to the reaction mixture, and the distribution coefficient of 2-octanone, a polyoxyalkylene compound and a copper chloride into the n-hexane layer:

$$\left( \frac{\text{weight percentage of each component in the n-hexane layer}}{\text{weight percentage of each component in the aqueous layer}} \right)$$

is shown in Table 1. The reaction mixture was apparently uniform and no deposition of the catalyst component on the wall of the reactor was observed through the reaction period.

EXAMPLES 2-3 AND CONTROLS 1-8

The polyoxyalkylene compound or water-soluble polar solvent of the variety and in the concentration shown in Table 1 or sodium lauryl benzene sulfonate (emulsifier) was used in place of $CH_3O(C_2H_4O)_{13}CH_3$ in Example 1, and the oxidation of 1-octene was carried out under the same conditions as in Example 1. Results of the reaction in our hour and those of the separation of the formed 2-octanone from the reaction mixture by steam distillation or by extraction with n-hexane are shown also in Table 1. Control 8 in Table 1 shows the case that the reaction was carried out using ferric chloride (6.0 mmol) in lieu of cupric chloride in Example 1.

TABLE 1

| | | Preparation of 2-octanone from 1-octene | | | | | | | |
|---|---|---|---|---|---|---|---|---|---|
| | Polyoxyalkylene glycols | | | | Steam distillation | | Distribution coefficient in n-hexane extraction | | |
| | | Concentration of | 2-octanone | | | Amount of | | | |
| Example or Control | Structure | aqueous solution (wt.%) | Yield (m mol) | Selectivity (%) | $H_2O(g)$/ 2-octanone (g) | distilled solvent (%)* | 2-octanone | Polyoxyalkylene glycols | Copper chloride |
| Example 1 | $CH_3O(C_2H_4O)_{13}CH_3$ | 50 | 31.5 | 96 | 3.75 | none | 75 | below 0.006 | below 0.001 |
| Example 2 | $C_2H_5O(C_2H_4O)_{23}C_2H_5$ | 50 | 30.0 | 96 | 3.96 | " | 75 | below 0.006 | below 0.001 |
| Example 3 | $CH_3O(C_2H_4O)_9CH_3$ | 40 | 25.0 | 96 | 3.90 | " | 79 | below 0.006 | below 0.001 |
| Control 1 | — | — | 3.2 | 73 | — | — | — | — | — |
| Control 2 | $CH_3O(C_2H_4O)_{13}CH_3$ | 15 | 10.0 | 85 | 4.15 | none | about 90 | below 0.006 | below 0.001 |
| Control 3 | $CH_3O(C_2H_4O)_{13}CH_3$ | 85 | 9.0 | 87 | above 10 | none | 5 | 0.024 | below 0.001 |
| Control 4 | dimethylformamide | 50 | 42.2 | 96 | 5.7 | 4.3 | 15 | | 0.009 |
| Control 5 | Sulfolane | 50 | 13.5 | 91 | — | not determined | 12 | | 0.005 |
| Control 6 | $C_3H_7O(C_2H_4O)_9C_3H_7$ | 50 (insoluble) | 19.5 | 96 | 15.4 | none | 49 | 0.127 | 0.008 |
| Control 7 | sodium laurylbenzenesulfonate | 0.8 | 8.0 | 89 | — | " | — | | not determined |
| Control 8 | $CH_3O(C_2H_4O)_9CH_3$ | 50 | 4.0 | 88 | — | " | — | not determined | not determined |

*based on the total amount of the solvent used.

TABLE 2

Preparation of phenylacetaldehyde from styrene

| Example or Control | Polyoxyalkylene glycol Structure | Concentration in aqueous solution (wt.%) | Phenylacetaldehyde Yield (m mol) | Phenylacetaldehyde Selectivity (%) | Selectivity to acetophenone (%) | Deposition of catalyst component on wall of reactor |
|---|---|---|---|---|---|---|
| Example 9 | $C_2H_5O(C_2H_4O)_{13}C_2H_5$ | 50 | 18.2 | 65 | 20 | none |
| Example 10 | $CH_3O(C_2H_4O)_{23}CH_3$ | 55 | 18.0 | 64 | 21 | none |
| Control 9 | — | — | 5.3 | 20 | 9 | observed |
| Control 10 | dimethylformamide | 50 | 17.2 | 62 | 25 | observed |
| Control 11 | sodium lauryl-benzenesulfonate | 0.34 | 6.1 | 58 | 30 | observed |
| Control 12 | $C_8H_{17}O(C_2H_4O)_{13}C_8H_{17}$ | 50 (insoluble) | 0.9 | 45 | 55 | none |

EXAMPLE 4

Into the same reactor as used in Example 1 were added distilled water (50 g),

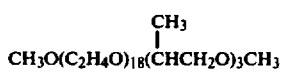

(50 g), palladous chloride (1.0 mmol) and cupric chloride (6.0 mmol), and the resultant mixture was heated at 80° C. under stirring. When the inner temperature became constant at 80° C., 2-octene (65 mmol) was added to the mixture, which was reacted for 1 hour under vigorous stirring while introducing oxygen gas at a rate of 5 l/hr. After the reaction, the reaction mixture was subjected to gas chromatographic analysis to obtain the results as follows:

Conversion of 2-octene=23%; yield of 2-octanone=10 mmol; yield of 3-octanone=4.5 mmol.

EXAMPLE 5

Into the same reactor as in Example 1 were added distilled water (40 g), $CH_3O(C_2H_4O)_{23}CH_3$ (60 g), palladous chloride (2.0 mmol), cupric chloride (4.0 mmol) and cuprous chloride (2.0 mmol), and the resultant mixture was heated under stirring to 85° C. When the inner temperature became constant at 85° C., 75 wt. % solution of norbornene in toluene (0.5 g) was added intermittently in one hour under vigorous stirring while introducing oxygen gas at a rate of 2.0 l/hr. Gas chromatographic analysis of the reaction mixture showed that the amount of the formed norbornanone was 0.8 mmol.

EXAMPLE 6

Into the same reaction apparatus as in Example 1 were fed distilled water (50 g), $C_2H_5O(C_2H_4O)_{18}C_2H_5$ (50 g), palladous chloride (2.0 mmol) and cupric chloride (16 mmol), and the resultant mixture was heated to 65° C. under stirring. When the inner temperature became constant at 65° C., 1,11-dodecadiene (15 mmol) was added while introducing oxygen gas at a rate of 2.0 l/hr to the mixture. The reaction was continued at the same temperature for 2 hours under vigorous stirring. Progress of the reaction was followed with gas chromatography at different times and the reaction was found to be a successive reaction. After two hours of reaction, the yield of 2,11-dodecadione was 2.5 mmol and the yield of 1-dodecen-11-one was 5.0 mmol.

EXAMPLE 7

Into the same reaction apparatus as in Example 1 were fed distilled water (30 g), $C_2H_5O(C_2H_4O)_{23}CH_3$ (70 g), palladous acetate (1.0 mmol), cupric chloride (6.0 mmol) and lithium chloride (2.0 mmol), and the resultant mixture was heated to 80° C. under stirring. When the inner temperature became constant at 80° C., 1-hexadecene (5 ml) (17.4 mmol) was continuously added through a microfeeder in one hour under vigorous stirring while introducing oxygen gas at a rate of 5 l/hr. After one hour the yield of 2-hexadecanone was 8.7 mmol.

EXAMPLE 8

Into the same reaction apparatus as in Example 1 was added distilled water (55 g), $C_2H_5O(C_2H_4O)_{18}CH_3$ (45 g), palladous chloride (7.5 mmol) and cupric chloride (15 mmol) and the resultant mixture was heated to 70° C. under stirring. When the inner temperature became constant at 70° C., 6-methyl-1,5-heptadiene (10 ml) (67.5 mmol) was added while introducing air at a rate of 5 l/hr to the mixture. The reaction was continued for 1.5 hour under vigorous stirring. Yield of 6-methyl-5-hepten-2-one was 28 mmol.

EXAMPLE 9

Into the same reaction apparatus as in Example 1 was added distilled water (50 g), $C_2H_5O(C_2H_4O)_{13}C_2H_5$ (50 g), palladium chloride (10 mmol) and cupric chloride (50 mmol), and the resultant mixture was heated to 80° C. under stirring in nitrogen atmosphere. When the inner temperature became constant at 80° C., styrene (35 mmol) was added to the mixture and the reaction was carried out under stirring in a nitrogen atmosphere for 30 minutes. No deposition of the catalyst component on the wall of the reactor was observed through the reaction period. After the reaction, the reaction mixture was subjected to gas chromatographic analysis to obtain the results shown in Table 2.

EXAMPLE 10 AND CONTROLS 9-12

Using a polyoxyalkylene glycol diether, water-soluble polar solvent or surfactant of the variety and in the concentration shown in Table 2 in place of the polyoxyalkylene compound used in Example 9 or without such additives, the oxidation of styrene was carried out under the same conditions as in Example 9. Results are shown in Table 2.

EXAMPLE 11

Into the same reaction apparatus as in Example 1 were fed distilled water (50 g), $CH_3O(C_2H_4O)_{13}C_2H_5$ (50 g), palladium chloride (1.0 mmol) and cupric chloride (8.0 mmol), and the resultant mixture was heated to 60° C. under stirring. When the inner temperature became constant at 60° C., 1-octene was added continuously at a rate of 20 mmol/hr through a microfeeder under vigorous stirring while introducing oxygen gas at a rate of 2.0 l/hr. The reaction was continued for 2.0 hours under these conditions. After cooling to room temperature, all the reaction mixture was poured into a separating funnel (capacity=300 ml) and extracted twice with 50 ml each of n-hexane. The n-hexane layers were combined and analyzed by gas chromatography to show 20 mmol of the extracted 2-octanone and 18 mmol of unreacted 1-octene. The residual aqueous layer was found to contain 2-octanone (0.9 mmol) and 1-octene (below 0.2 mmol). Total remaining aqueous layer was again fed into the above reaction apparatus and the reaction was carried out at 60° C. for 2 hours while introducing continuously oxygen gas and 1-octene at the same rate as in the first run. After the reaction, the reaction mixture was extracted twice with 50 ml of n-hexane. The n-hexane layer contained 18.5 mmol of 2-octanone and 19.5 mmol of 1-octene. The residual layer was again fed into the said reaction apparatus, and the reaction and extraction were repeated as above described. Thus, 17.0 mmol of 2-octanone and 21.5 mmol of 1-octene were determined in the n-hexane layer.

EXAMPLE 12

The reaction was carried out repeatedly in the same manner as in Example 11, except that steam distillation was employed in place of extraction with n-hexane for separating the product and unreacted material from the reaction mixture. The quantity of the aqueous solution in the reaction system was kept nearly constant by supplying the distilled water before the start of each reaction in an amount balancing the water distilled off during the period of steam distillation. The steam distillation was adjusted so as to keep 93 to 96% (based on total 2-octanone formed) of 2-octanone existing in the distillate in each run. Determination of water, 2-octanone and 1-octene contained in the distillate in each run gave the following results.

1st Run: water (14.4 g), 2-octanone (19 mmol) and 1-octene (18 mmol)

2nd Run: water (14.6 g), 2-octanone (17.8 mmol) and 1-octene (19 mmol)

3rd Run: water (15.0 g), 2-octanone (16.5 mmol) and 1-octene (21 mmol)

EXAMPLE 13

Into a 2 l four-necked flask equipped with a thermometer, a stirrer, a reflux condenser and a gas-inlet were fed palladous chloride (17.73 g), cupric chloride dihydrate (85.24 g), $CH_3O(C_2H_4O)_{23}CH_3$ (500 g) and water (500 g), and the resultant mixture was heated to 80° C. under stirring while purging the flask with nitrogen gas. When the inner temperature became constant at 80° C., styrene (36.4 g) was added to the mixture, which was stirred vigorously in a nitrogen atmosphere for 30 minutes. Thirty minutes later the formation of palladium black was observed but no deposition thereof on the wall of the reactor was observed. The reaction mixture was cooled at temperature below 40° C. and mixed with 500 ml of toluene. After stirring for 10 minutes, the mixture was allowed to stand. The light yellow toluene layer was separated. The aqueous layer was extracted twice with 500 ml each of toluene.

After the extraction with toluene, the aqueous residual layer containing the catalyst component and $CH_3O(C_2H_4O)_{23}CH_3$ was subjected to regeneration of the catalyst by introducing oxygen gas at a rate of 20 l/hr into the aqueous layer in said flask under stirring with the temperature being raised to 40°-50° C. The palladium black disappeared during this reaction to give a uniform solution. After the system was purged with nitrogen gas, styrene (36.4 g) was again added to the aqueous solution containing the regenerated catalyst. The reaction was carried out at 80° C. for 30 minutes under stirring. After the reaction, the reaction mixture was extracted three times with 500 ml each of toluene as above described. The aqueous residual layer was treated in the same procedures and conditions as above described to regenerate the catalyst. To the aqueous solution containing the regenerated catalyst was added styrene (36.4 g) again, and the reaction was carried out at 80° C. for 30 minutes. The reaction mixture was extracted three times with 500 ml each of toluene.

The toluene layers (about 4.7 l) were collected and the toluene was evaporated under reduced pressure. The residual liquid was fed to a fractionating column under reduced pressure. Thus, the remaining toluene was at first evaporated, then styrene (35 g) was recovered at 35° C./10 mmHg and fractional distillation was further conducted at 100° to 110° C. (bath temperature) to obtain a distillate (73 g) boiling at 45° to 50° C./2 mmHg. This distillate was found to be a mixture of phenylacetaldehyde (78 wt.%), acetophenone (19 wt.%) and benzaldehyde (3 wt.%) according to gas chromatographic analysis. The thus obtained mixture, 100 ml of toluene and 5 g of Raney nickel catalyst modified with molybdenum (Mo/Ni=6/94 atomic ratio) were fed into an autoclave of 500 ml capacity equipped with a magnetic stirrer, and hydrogenation was carried out at room temperature under 500 atm. of hydrogen pressure for 20 hours. After the reaction, the catalyst was filtered off from the reaction mixture. The filtrate was evaporated to remove the toluene by a rotary evaporator. The remaining liquid was subjected to fractional distillation under reduced pressure of 10 mmHg, whereby benzyl alcohol (1.8 g) boiling at 75° C./10 mmHg, α-phenethyl alcohol (13.1 g) boiling at 87° C./10 mmHg and β-phenethyl alcohol (53.8 g) boiling at 97° C./10 mmHg were obtained. Thus-obtained β-phenethyl alcohol had a refraction index $n_D^{20}=1.533$ and no halogen according to halogen-detective test and showed no other peaks on the gas chromatogram.

EXAMPLE 14

Into a four-necked cylindrical flask of 2 l capacity equipped with a thermometer, a stirrer, a reflux condenser and a gas-inlet was fed palladous chloride (35.4 g), cuprous chloride (5.0 g), cupric chloride dihydrate (93.5 g), $HO(C_2H_4O)_{10}H$ (525 g) and distilled water (475 g), and the resultant mixture was heated to 75° C. under stirring while purging the flask with nitrogen gas. When the inner temperature became constant at 75° C., toluene (50 ml) and styrene (46.8 g) were added to the mixture, which was then stirred vigorously for 20 minutes in a nitrogen atmosphere. The formation of palladium black was observed in about 10 minutes but no deposition of palladium black on the wall of the reactor was observed. The reaction mixture was cooled to room temperature inside, mixed with toluene (300 ml), stirred for 10 minutes and allowed to stand. The separated light yellow toluene layer (350 ml) was recovered. The remaining aqueous layer was twice extracted with toluene by adding 300 ml of toluene to the aqueous layer and stirring the mixture for 10 minutes (total toluene layer collected, about 950 ml; the toluene layer remaining in aqueous solution containing the catalyst, about 50 ml). Total toluene layer collected was put in a separating funnel and washed with 20 ml of water. The aqueous washing was subjected to distillation to remove 18 ml of water and the residue was combined with the above aqueous layer (aqueous catalyst solution) originating from the toluene extraction. Thereafter oxygen gas was bubbled at a rate of 10 l/hr into the aqueous catalyst solution at 40° C. under stirring for 90 minutes to regenerate the catalyst. By this treatment the precipitate of palladium black disappeared resulting in a uniform solution. Then the flask was purged with nitrogen gas, and styrene (46.8 g) was again added to the aqueous solution containing regenerated catalyst. The oxidation reaction was carried out at 75° C. for 20 minutes under stirring. The reaction mixture was extracted with 300 ml of toluene three times as above described. The separated toluene layer (total quantity of about 950 ml) was washed with water (20 ml). The aqueous washing was subjected to evaporation under reduced pressure to remove 18 ml of water and was combined with the above aqueous layer after extraction with toluene. Then said aqueous layer was subjected to regeneration of the catalyst at 40° C. for 90 minutes at a rate of 10 l/hr of oxygen gas. The same procedure was repeated once more. The separated toluene layer (total: about 1.92 l) after washing with water was fed together with 250 ml of 0.1 N aqueous solution of sodium hydroxide into a three-necked flask of 5 l capacity and stirred at 60° C. in a carbon monoxide atmosphere for 30 minutes, whereby the palladium salt contained in the toluene layer was converted into palladium black. After the palladium black precipitate was filtered off and each 5 ppm (based on the weight of the toluene solution) of t-butylcatechol and triphenyl phosphite were added to the toluene solution. Then, the mixture was put in a distillation apparatus to first distill off the toluene at 45° to 50° C. followed by the distillation of styrene (46.7 g) at 35° C./10 mmHg. Fractional distillation was carried out at 95° to 105° C. (bath temperature) give a distillate (100 g) boiling at 45° to 50° C./2 mmHg. This distillate was a mixture of phenylacetaldehyde (82 weight %), acetophenone (16 weight %), benzaldehyde (1 weight %) and other materials (1 weight %) according to gas chromatographic analysis.

What we claim is:

1. A process for producing a carbonyl compound which comprises: oxidizing under aqueous Wacker oxidation conditions a monoolefinic hydrocarbon or a non-conjugated diolefinic hydrocarbon having 6 to 25 carbon atoms in an aqueous medium containing palladium or a salt thereof as a catalyst and a copper salt as a redox promoter in the presence of a water-soluble polyoxyalkylene compound of the formula

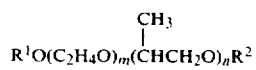 (I)

wherein each of $R^1$ and $R^2$ represents either a hydrogen atom or a hydrocarbon radical having 1 to 8 carbon atoms; m is an integer greater than zero and n is zero or an integer greater than zero, such that $m+n \geq 4$ and $m > 3$ n, said polyoxyalkylene compound being used in a proportion of about $\frac{1}{4}$ to about 3 parts by weight per one part by weight of water in the reaction system; and recovering a carbonyl compound corresponding in number of carbon atoms to the starting olefinic hydrocarbon.

2. Process according to claim 1, in which the oxidation is carried out at a temperature from room temperature to about 150° C.

3. Process according to claim 2, in which $R^1$ and $R^2$ of the polyoxyalkylene compound in the formula (I) are each selected from the group consisting of a hydrogen atom and an alkyl group containing 1 to 5 carbon atoms.

4. A process according to claim 1, in which n is zero and m is 6 to 75 in the formula (I).

5. Process according to claim 1, in which the palladium or salt thereof is selected from the group consisting of metallic palladium, palladium chloride, palladium bromide, palladium nitrate, palladium acetate, palladium bromide, palladium nitrate, palladium acetate, palladium-lithium chloride, and palladium-sodium chloride, and is used in an amount of 0.001 to 0.5 mol per 1 l of the reaction system.

6. Process according to claim 1, in which the copper salt is selected from the group consisting of cuprous chloride, cuprous bromide, cuprous oxide, cupric chloride, cupric bromide, cupric acetate, cupric nitrate and cupric oxide, and is used in an amount of 1 to 50 in terms of atomic ratio of copper to palladium.

7. Process according to claim 1, in which the oxidation is carried out in an atmosphere of oxygen-containing gas.

8. Process according to claim 1, in which the oxidation is carried out in the substantial absence of oxygen-containing gas, and the aqueous layer containing the catalyst component separated from the reaction mixture is contacted with an oxygen-containing gas thereby reoxidizing the catalyst, and then the said aqueous layer is recycled to the oxidation of the olefinic hydrocarbon.

9. Process according to claim 1, in which the recovery of the carbonyl compound is achieved by steam distillation of the reaction mixture.

10. Process according to claim 1, in which the recovery of the carbonyl compound is achieved by solvent-extraction of the reaction mixture.

11. Process according to claim 1, in which styrene is oxidized in the substantial absence of oxygen-containing gas in an aqueous medium containing palladium or salt thereof and a cupric salt in the presence of a polyoxyethylene compound of formula (I) wherein $R^1$ and $R^2$ are each a hydrogen atom or an alkyl group having 1 to 5 carbon atoms, n is zero and m is 6 to 75, thereby forming phenylacetaldehyde.

12. Process according to claim 11, in which the phenylacetaldehyde formed is recovered from the reaction mixture by solvent-extraction and the aqueous residual layer is contacted with an oxygen-containing gas thereby reoxidizing the catalyst component and then recycled to the oxidation reaction.

13. Process according to claim 12, in which the phenylacetaldehyde formed is hydrogenated to prepare β-phenethyl alcohol.

* * * * *